US010406329B2

United States Patent
Wilson et al.

(10) Patent No.: US 10,406,329 B2
(45) Date of Patent: Sep. 10, 2019

(54) THROUGH TIP FOR CATHETER

(75) Inventors: Bruce M. Wilson, Temecula, CA (US);
Kerry J. Williams, Temecula, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 720 days.

(21) Appl. No.: 13/481,532

(22) Filed: May 25, 2012

(65) Prior Publication Data
US 2012/0302994 A1 Nov. 29, 2012

Related U.S. Application Data

(60) Provisional application No. 61/490,444, filed on May 26, 2011.

(51) Int. Cl.
*A61M 25/10* (2013.01)

(52) U.S. Cl.
CPC ...... *A61M 25/1006* (2013.01); *A61M 25/104* (2013.01); *A61M 2025/1061* (2013.01); *A61M 2025/1093* (2013.01); *Y10T 29/49826* (2015.01)

(58) Field of Classification Search
CPC ............ A61M 25/1006; A61M 25/104; A61M 2025/1093; A61M 2025/1061; A61M 25/10; A61M 25/104098; A61F 2/958
USPC ......... 606/194, 108, 192, 191, 159, 198, 28; 604/506, 96.01, 103, 103.1
See application file for complete search history.

(56) References Cited

U.S. PATENT DOCUMENTS

| 4,425,919 | A |   | 1/1984 | Alston, Jr. et al. |
| 4,563,181 | A |   | 1/1986 | Wijayarathna et al. |
| 4,596,563 | A |   | 6/1986 | Pande |
| 4,721,117 | A | * | 1/1988 | Mar ............... A61M 25/09033 600/585 |

(Continued)

FOREIGN PATENT DOCUMENTS

| EP | 0 277 368 A | 8/1988 |
| EP | 0414350 | 2/1991 |

(Continued)

OTHER PUBLICATIONS

Cordis' Product Brochure; The Journey Inspires the Design, AQUA T3, Dec. 2002.

(Continued)

*Primary Examiner* — Vi X Nguyen
(74) *Attorney, Agent, or Firm* — Baker Botts L.L.P.

(57) ABSTRACT

Catheter having an elongate tubular shaft including an inflation lumen and a guidewire lumen defined therein, the guidewire lumen extending along at least a distal length of an inner tubular member of the elongate tubular shaft. The catheter includes a distal tip member having a proximal end and a distal end, wherein the distal tip member is monolithic and the proximal end of the distal tip member is secured to a distal end of the inner tubular member. The catheter includes a balloon having a proximal portion and a distal portion, the proximal portion of the balloon sealingly coupled to the distal portion of the elongate tubular shaft. The distal portion of the balloon is sealingly coupled to the distal tip member and the balloon defines an inner chamber in communication with the inflation lumen, wherein the proximal end of the distal tip member is disposed within the inner chamber.

25 Claims, 6 Drawing Sheets

(56) References Cited

U.S. PATENT DOCUMENTS

| | | |
|---|---|---|
| 4,775,371 A | 10/1988 | Mueller, Jr. |
| 4,782,834 A | 11/1988 | Maguire et al. |
| 4,820,349 A | 4/1989 | Saab et al. |
| 4,877,031 A | 10/1989 | Conway et al. |
| 4,886,506 A | 12/1989 | Lovgren et al. |
| 4,892,519 A | 1/1990 | Songer et al. |
| 4,952,357 A | 8/1990 | Euteneuer |
| 4,976,690 A | 12/1990 | Solar et al. |
| 4,976,720 A | 12/1990 | Machold et al. |
| 5,047,045 A | 9/1991 | Arney et al. |
| 5,061,273 A | 10/1991 | Yock |
| 5,078,702 A | 1/1992 | Pomeranz |
| 5,085,649 A | 2/1992 | Flynn |
| 5,112,304 A | 5/1992 | Barlow et al. |
| 5,156,594 A | 10/1992 | Keith |
| 5,176,661 A | 1/1993 | Evard et al. |
| 5,195,969 A | 3/1993 | Wang et al. |
| 5,205,822 A | 4/1993 | Johnson et al. |
| 5,207,700 A | 5/1993 | Euteneuer |
| 5,217,434 A | 6/1993 | Arney |
| 5,217,482 A | 6/1993 | Keith |
| 5,250,059 A | 10/1993 | Andreas et al. |
| 5,256,144 A * | 10/1993 | Kraus ................ A61M 25/104 604/913 |
| 5,270,086 A | 12/1993 | Hamlin |
| 5,277,199 A | 1/1994 | DeBois et al. |
| 5,290,232 A | 3/1994 | Johnson et al. |
| 5,290,306 A | 3/1994 | Trotta et al. |
| 5,300,025 A | 4/1994 | Wantink |
| 5,304,134 A * | 4/1994 | Kraus et al. ............. 604/96.01 |
| 5,312,430 A | 5/1994 | Rosenbluth et al. |
| 5,318,032 A | 6/1994 | Lonsbuty et al. |
| 5,318,526 A | 6/1994 | Cohen |
| 5,342,386 A | 8/1994 | Trotta |
| 5,358,486 A | 10/1994 | Saab |
| 5,364,357 A | 11/1994 | Aase |
| 5,370,655 A | 12/1994 | Burns |
| 5,378,238 A | 1/1995 | Peters et al. |
| 5,395,336 A | 3/1995 | Barclay et al. |
| 5,423,754 A | 6/1995 | Cornelius et al. |
| 5,425,712 A | 6/1995 | Goodin |
| 5,447,497 A | 9/1995 | Sogard et al. |
| 5,451,233 A | 9/1995 | Yock |
| 5,454,789 A | 10/1995 | Burns et al. |
| 5,458,615 A | 10/1995 | Klemm et al. |
| 5,470,315 A | 11/1995 | Adams |
| 5,476,477 A | 12/1995 | Burns |
| 5,478,320 A | 12/1995 | Trotta |
| 5,484,409 A | 1/1996 | Atkinson et al. |
| 5,490,837 A | 2/1996 | Blaeser et al. |
| 5,496,275 A | 3/1996 | Sirhan et al. |
| 5,499,980 A | 3/1996 | Euteneuer |
| 5,507,768 A | 4/1996 | Lau et al. |
| 5,512,051 A | 4/1996 | Wang et al. |
| 5,526,823 A | 6/1996 | Wheeler et al. |
| 5,538,513 A | 7/1996 | Okajima |
| 5,545,134 A | 8/1996 | Hilaire et al. |
| 5,549,552 A | 8/1996 | Peters et al. |
| 5,554,121 A | 9/1996 | Ainsworth et al. |
| 5,556,383 A | 9/1996 | Wang et al. |
| 5,569,195 A | 10/1996 | Saab |
| 5,587,125 A | 12/1996 | Roychowdhury |
| 5,599,326 A | 2/1997 | Carter |
| 5,613,979 A | 3/1997 | Trotta et al. |
| 5,620,649 A | 4/1997 | Trotta |
| 5,622,665 A | 4/1997 | Wang |
| 5,632,760 A | 5/1997 | Sheiban et al. |
| 5,643,209 A | 7/1997 | Fugoso et al. |
| 5,649,909 A | 7/1997 | Cornelius |
| 5,658,264 A | 8/1997 | Samson |
| 5,690,613 A | 11/1997 | Verbeek |
| 5,728,063 A | 3/1998 | Preissman et al. |
| 5,743,874 A | 4/1998 | Fischell et al. |
| 5,743,875 A | 4/1998 | Sirhan et al. |
| 5,749,849 A | 5/1998 | Engelson |
| 5,755,690 A | 5/1998 | Saab |
| 5,759,173 A | 6/1998 | Preissman et al. |
| 5,766,151 A | 6/1998 | Valley et al. |
| 5,769,817 A | 6/1998 | Burgmeier |
| 5,769,819 A | 6/1998 | Schwab et al. |
| 5,775,327 A | 7/1998 | Randolph et al. |
| 5,779,731 A | 7/1998 | Leavitt |
| 5,782,811 A | 7/1998 | Samson et al. |
| 5,791,036 A | 8/1998 | Goodin et al. |
| 5,792,124 A | 8/1998 | Horrigan et al. |
| 5,792,144 A | 8/1998 | Fischell et al. |
| 5,795,325 A | 8/1998 | Valley et al. |
| 5,795,341 A | 8/1998 | Samson |
| 5,797,887 A | 8/1998 | Rosen et al. |
| 5,814,016 A | 9/1998 | Valley et al. |
| 5,820,594 A | 10/1998 | Fontirroche et al. |
| 5,833,657 A | 11/1998 | Reinhardt et al. |
| 5,879,369 A | 3/1999 | Ishida |
| 5,879,499 A | 3/1999 | Corvi |
| 5,902,290 A | 5/1999 | Peacock et al. |
| 5,908,406 A | 6/1999 | Ostapchenko et al. |
| 5,911,715 A | 6/1999 | Berg et al. |
| 5,916,193 A | 6/1999 | Stevens et al. |
| 5,947,939 A | 9/1999 | Mortier et al. |
| 5,964,778 A | 10/1999 | Fugoso et al. |
| 6,004,289 A | 12/1999 | Saab |
| 6,004,339 A | 12/1999 | Wijay |
| 6,010,521 A | 1/2000 | Lee et al. |
| 6,021,340 A | 2/2000 | Randolph et al. |
| 6,024,693 A | 2/2000 | Schock et al. |
| 6,024,722 A | 2/2000 | Rau et al. |
| 6,027,510 A | 2/2000 | Alt |
| 6,036,670 A | 3/2000 | Wijeratne et al. |
| 6,056,719 A | 5/2000 | Mickley |
| 6,059,751 A | 5/2000 | Ostapchenko et al. |
| 6,059,770 A | 5/2000 | Peacock et al. |
| 6,071,266 A | 6/2000 | Kelley |
| 6,086,556 A | 7/2000 | Hamilton et al. |
| 6,102,890 A | 8/2000 | Stivland et al. |
| 6,124,007 A | 9/2000 | Wang et al. |
| 6,132,824 A | 10/2000 | Hamlin |
| 6,136,258 A | 10/2000 | Wang et al. |
| 6,146,356 A | 11/2000 | Wang et al. |
| 6,165,166 A | 12/2000 | Samuelson et al. |
| 6,165,195 A | 12/2000 | Wilson et al. |
| 6,168,588 B1 | 1/2001 | Wilson |
| 6,171,275 B1 | 1/2001 | Webster, Jr. et al. |
| 6,171,278 B1 | 1/2001 | Wang et al. |
| 6,179,810 B1 | 1/2001 | Wantink et al. |
| 6,179,856 B1 | 1/2001 | Barbere |
| 6,193,686 B1 | 2/2001 | Estrada et al. |
| 6,197,015 B1 | 3/2001 | Wilson |
| 6,210,396 B1 | 4/2001 | MacDonald et al. |
| 6,217,565 B1 | 4/2001 | Cohen |
| 6,242,063 B1 | 6/2001 | Ferrera et al. |
| 6,245,053 B1 | 6/2001 | Benjamin |
| 6,251,093 B1 | 6/2001 | Valley et al. |
| 6,264,063 B1 | 7/2001 | Stack et al. |
| 6,265,016 B1 | 7/2001 | Hostettler et al. |
| 6,306,097 B1 | 10/2001 | Park et al. |
| 6,306,124 B1 | 10/2001 | Jones et al. |
| 6,308,342 B1 | 10/2001 | Xiaoming |
| 6,358,227 B1 | 3/2002 | Ferrera et al. |
| 6,364,894 B1 | 4/2002 | Healy et al. |
| 6,416,494 B1 | 7/2002 | Wilkins |
| 6,482,348 B1 | 11/2002 | Wang et al. |
| 6,495,090 B1 | 12/2002 | Wilkins et al. |
| 6,495,127 B1 | 12/2002 | Wallace et al. |
| 6,500,148 B1 | 12/2002 | Pinchuck et al. |
| 6,508,784 B1 | 1/2003 | Shu |
| 6,575,934 B2 | 6/2003 | Duchamp |
| 6,575,958 B1 | 6/2003 | Happ et al. |
| 6,579,259 B2 | 6/2003 | Stevens et al. |
| 6,585,687 B1 | 7/2003 | Shkolnik |
| 6,585,688 B2 | 7/2003 | Ferrera et al. |
| 6,589,207 B1 | 7/2003 | El-Nounou |
| 6,589,226 B1 | 7/2003 | Owens |
| 6,620,127 B2 | 9/2003 | Lee et al. |
| 6,620,128 B1 | 9/2003 | Simhambhatla |

(56) References Cited

U.S. PATENT DOCUMENTS

| | | | |
|---|---|---|---|
| 6,626,889 B1 | 9/2003 | Simpson et al. |
| 6,629,961 B1 | 10/2003 | Israelsson et al. |
| 6,645,422 B2 | 11/2003 | Jung, Jr. et al. |
| 6,663,614 B1 | 12/2003 | Carter |
| 6,673,291 B1 | 1/2004 | Field et al. |
| 6,673,302 B2 | 1/2004 | Wang et al. |
| 6,695,809 B1 | 2/2004 | Lee |
| 6,702,802 B1 | 3/2004 | Hancock et al. |
| 6,718,211 B2 | 4/2004 | Smits |
| 6,733,487 B2 | 5/2004 | Keith et al. |
| 6,756,094 B1 | 6/2004 | Wang et al. |
| 6,777,644 B2 | 8/2004 | Peacock et al. |
| 6,793,647 B1 | 9/2004 | Cryer et al. |
| 6,796,958 B2 | 9/2004 | Chen et al. |
| 6,796,960 B2 | 9/2004 | Cioanta et al. |
| 6,835,189 B2 | 12/2004 | Musbach et al. |
| 6,837,890 B1 | 1/2005 | Chludzinski et al. |
| 6,863,678 B2 | 3/2005 | Lee et al. |
| 6,875,197 B1 | 4/2005 | Simhambhatla et al. |
| 6,887,219 B2 | 5/2005 | Wantink |
| 6,890,395 B2 | 5/2005 | Simhambhatla et al. |
| 6,893,456 B2 | 5/2005 | Lumauig |
| 6,911,038 B2 | 6/2005 | Mertnes et al. |
| 6,913,600 B2 | 7/2005 | Valley et al. |
| 6,918,920 B1 | 7/2005 | Wang et al. |
| 6,923,822 B2 | 8/2005 | Crawford et al. |
| 6,946,092 B1 | 9/2005 | Bertolino et al. |
| 6,951,555 B1 | 10/2005 | Suresh et al. |
| 6,951,675 B2 | 10/2005 | Chin et al. |
| 6,964,750 B2 | 11/2005 | Fulford |
| 6,979,342 B2 | 12/2005 | Lee et al. |
| 7,026,026 B2 | 4/2006 | Ferrera et al. |
| 7,029,732 B2 | 4/2006 | Wang et al. |
| 7,037,291 B2 | 5/2006 | Lee et al. |
| 7,037,295 B2 | 5/2006 | Tieman et al. |
| 7,074,206 B2 | 7/2006 | Lee et al. |
| 7,108,877 B2 | 9/2006 | Blair et al. |
| 7,112,357 B2 | 9/2006 | Miller et al. |
| 7,141,059 B2 | 11/2006 | Duchamp et al. |
| 7,147,817 B1 | 12/2006 | Lim et al. |
| 7,163,523 B2 | 1/2007 | Devens, Jr. et al. |
| 7,195,638 B1 | 3/2007 | Sridharan |
| 7,273,485 B2 | 9/2007 | Simpson et al. |
| 7,303,798 B2 | 12/2007 | Bavaro et al. |
| 7,322,959 B2 | 1/2008 | Warnack et al. |
| 7,335,185 B2 | 2/2008 | Tang et al. |
| 7,341,571 B1 | 3/2008 | Harris et al. |
| 7,549,975 B2 | 6/2009 | Lee et al. |
| 7,556,634 B2 | 7/2009 | Lee et al. |
| 7,662,130 B2 | 2/2010 | Lee et al. |
| 7,828,766 B2 | 11/2010 | Durcan |
| 7,833,193 B2 | 11/2010 | Lee et al. |
| 7,833,597 B2 | 11/2010 | Bavaro et al. |
| 7,862,541 B2 | 1/2011 | Jeffrey et al. |
| 7,906,066 B2 | 3/2011 | Wilson et al. |
| 7,967,836 B2 | 6/2011 | Warnack et al. |
| 8,048,058 B2 | 11/2011 | Fulford |
| 8,052,638 B2 | 11/2011 | Lee et al. |
| 8,070,719 B2 | 12/2011 | Lee et al. |
| 2001/0001812 A | 1/2001 | Valley et al. |
| 2001/0029362 A1 | 10/2001 | Sirhan et al. |
| 2001/0037085 A1 | 11/2001 | Keith et al. |
| 2002/0018866 A1 | 2/2002 | Lee et al. |
| 2002/0082549 A1* | 6/2002 | Duchamp ......... A61M 25/1034 604/96.01 |
| 2002/0165523 A1 | 11/2002 | Chin et al. |
| 2003/0009151 A1 | 1/2003 | Wang |
| 2003/0032920 A1 | 2/2003 | Wantik |
| 2003/0055447 A1 | 3/2003 | Lee et al. |
| 2003/0055448 A1* | 3/2003 | Lee et al. ............... 606/192 |
| 2003/0105426 A1 | 6/2003 | Jorgensen |
| 2003/0139762 A1 | 7/2003 | Lee |
| 2004/0059291 A1 | 3/2004 | McDonnell et al. |
| 2004/0059292 A1 | 3/2004 | Hisamatsu et al. |
| 2004/0064130 A1 | 4/2004 | Carter |
| 2004/0068240 A1 | 4/2004 | Goodin et al. |
| 2004/0097892 A1 | 5/2004 | Evans et al. |
| 2004/0116956 A1* | 6/2004 | Duchamp et al. ............ 606/194 |
| 2004/0131808 A1 | 7/2004 | Schoenle et al. |
| 2004/0167441 A1 | 8/2004 | Reynolds et al. |
| 2004/0170782 A1 | 9/2004 | Wang et al. |
| 2004/0173935 A1 | 9/2004 | Lim et al. |
| 2004/0181206 A1 | 9/2004 | Chiu et al. |
| 2004/0191443 A1 | 9/2004 | Hamlin |
| 2004/0215141 A1 | 10/2004 | Clarke et al. |
| 2004/0267195 A1 | 12/2004 | Currlin |
| 2004/0267280 A1 | 12/2004 | Nishide et al. |
| 2005/0015048 A1 | 1/2005 | Chiu et al. |
| 2005/0043679 A1 | 2/2005 | Devens et al. |
| 2005/0148997 A1 | 2/2005 | Valley et al. |
| 2005/0124976 A1 | 6/2005 | Devens, Jr. et al. |
| 2005/0131445 A1 | 6/2005 | Holman et al. |
| 2005/0154414 A1 | 7/2005 | Perreault et al. |
| 2005/0186370 A1 | 8/2005 | Hamilton et al. |
| 2005/0228429 A1 | 10/2005 | Burgmeier et al. |
| 2005/0238833 A1 | 10/2005 | Wang et al. |
| 2005/0261725 A1 | 11/2005 | Crawford et al. |
| 2005/0277878 A1 | 12/2005 | Lee |
| 2006/0008606 A1 | 1/2006 | Horn et al. |
| 2006/0136032 A1 | 6/2006 | Legarda et al. |
| 2006/0165926 A1 | 7/2006 | Weber |
| 2006/0175739 A1 | 8/2006 | Hession et al. |
| 2006/0282041 A1 | 12/2006 | Melsheimer et al. |
| 2007/0016165 A1* | 1/2007 | Von Oepen ....... A61M 25/0021 604/525 |
| 2007/0021772 A1 | 1/2007 | von Oepen et al. |
| 2007/0060863 A1 | 3/2007 | Goeken et al. |
| 2007/0142771 A1 | 6/2007 | Durcan |
| 2007/0167973 A1 | 7/2007 | Stupecky et al. |
| 2007/0191813 A1 | 8/2007 | Chen |
| 2007/0240817 A1 | 10/2007 | Strong et al. |
| 2008/0015499 A1 | 1/2008 | Warnack |
| 2008/0045895 A1 | 2/2008 | Simpson et al. |
| 2008/0045928 A1 | 2/2008 | Simpson et al. |
| 2008/0065188 A1 | 3/2008 | Pallazza |
| 2008/0262470 A1 | 10/2008 | Lee et al. |
| 2009/0005754 A1 | 1/2009 | Soetermans |
| 2009/0036829 A1 | 2/2009 | Pagel et al. |
| 2009/0156998 A1* | 6/2009 | Arana et al. ................. 604/103 |
| 2009/0223624 A1 | 9/2009 | Lee et al. |
| 2009/0247946 A1 | 10/2009 | Lee et al. |
| 2009/0264822 A1 | 10/2009 | Johnson |
| 2010/0010439 A1 | 1/2010 | Burgmeier et al. |
| 2010/0130925 A1 | 5/2010 | Haslinger et al. |
| 2010/0189876 A1 | 7/2010 | Kokish et al. |
| 2010/0285085 A1 | 11/2010 | Stankus et al. |
| 2011/0022150 A1 | 1/2011 | Durcan |
| 2011/0070355 A1 | 3/2011 | Bavaro et al. |
| 2011/0172696 A1 | 7/2011 | Jeffrey et al. |
| 2011/0315301 A1 | 12/2011 | Simpson et al. |
| 2012/0065586 A1 | 3/2012 | Lee et al. |
| 2012/0143129 A1 | 6/2012 | Simpson et al. |

FOREIGN PATENT DOCUMENTS

| | | |
|---|---|---|
| EP | 0420488 | 3/1991 |
| EP | 0737487 | 10/1996 |
| EP | 0821979 | 2/1998 |
| EP | 0904795 | 3/1999 |
| EP | 0931558 | 7/1999 |
| EP | 0962227 | 8/1999 |
| EP | 1 103 280 A | 5/2001 |
| EP | 1 287 846 A | 3/2003 |
| JP | 10-290837 | 11/1998 |
| JP | 2001-353225 | 12/2001 |
| JP | 2005-167638 | 6/2005 |
| WO | WO/1989/002763 | 4/1989 |
| WO | WO 1993/020882 | 10/1993 |
| WO | WO 1995/018647 | 7/1995 |
| WO | WO 1996/003175 | 2/1996 |
| WO | WO 1996/034646 | 11/1996 |
| WO | WO 1999/013924 | 3/1999 |
| WO | WO 2001/034240 | 5/2001 |
| WO | WO 2001/051115 | 7/2001 |

(56) References Cited

FOREIGN PATENT DOCUMENTS

| WO | WO 2001/089621 | 11/2001 |
|----|----------------|---------|
| WO | WO 2002/036196 | 5/2002 |
| WO | WO/2003/004248 | 1/2003 |
| WO | WO 2005/021083 | 3/2005 |
| WO | WO 2006/0126311 | 11/2006 |
| WO | WO/2007/054364 | 5/2007 |
| WO | WO/2007/146572 | 12/2007 |

OTHER PUBLICATIONS

The Manufacturing Process Section of the Phelps Dodge High Performance Conductors Brochure, a Primer on Polymide Tubing, pp. 1.
http://www.zeusinc.com/peek_resin.asp.
www.sigmaaldrich.com/img/assets/3900/Thermal_Transitions_of_Homopolymers.pdf.
Etherington & Roberts Dictionary, http://Palimpsest.stanford.edu/don/dt/dt1549.html.
Polymers: Structure and Properties, C.A. Daniels, Ph.D., P.E.; Technomic Publishing Co., Inc.
International Search Report for PCT/US2010/037313, dated Apr. 28, 2011.
International Search Report and Written Opinion for PCT/US2012/039700, dated Oct. 5, 2012 (Corresponding to U.S. Appl. No. 13/481,532).

* cited by examiner

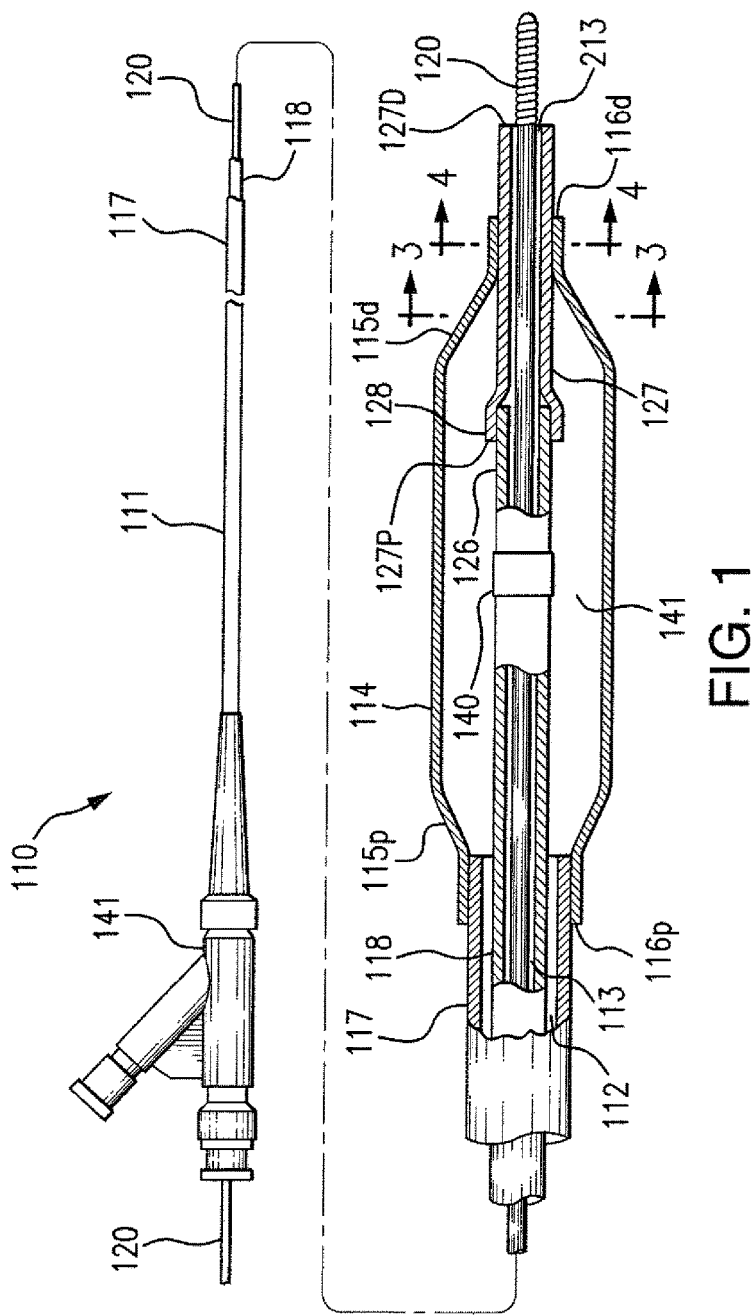
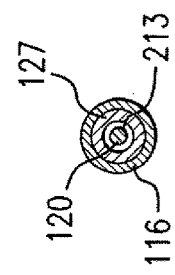
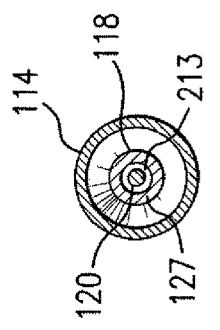
FIG. 1
FIG. 3
FIG. 4

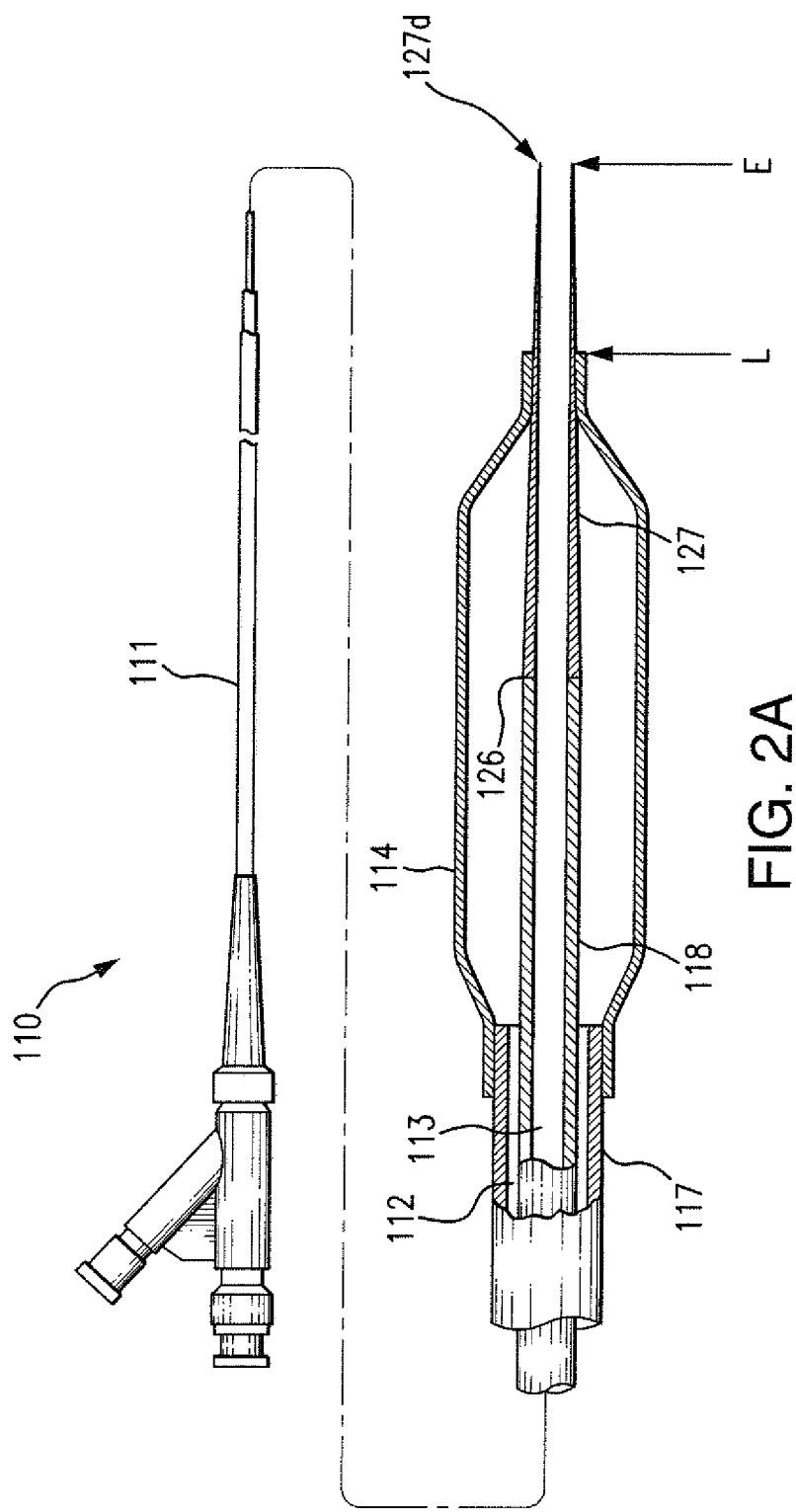

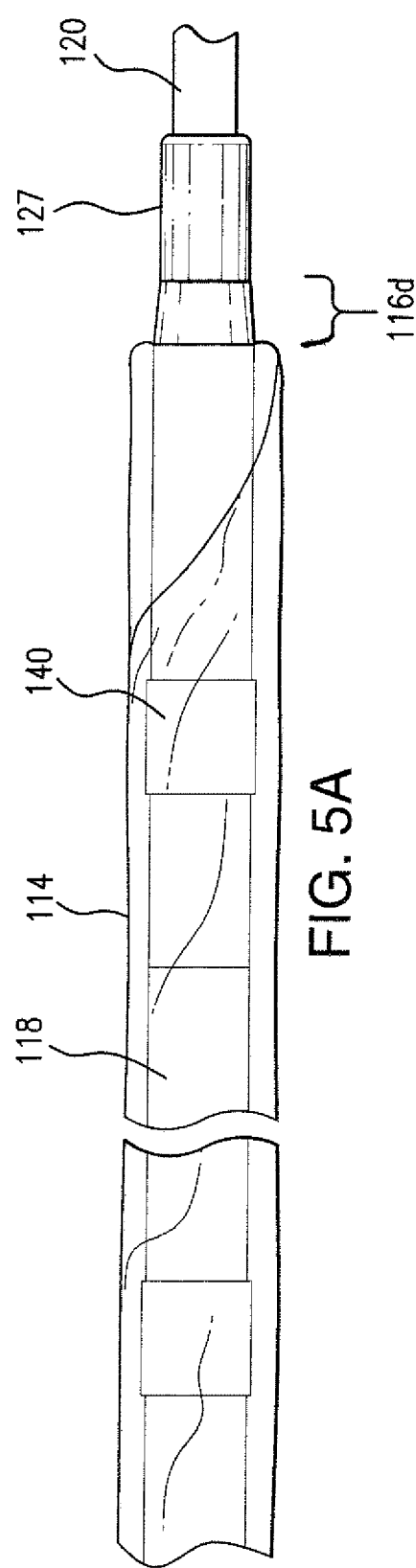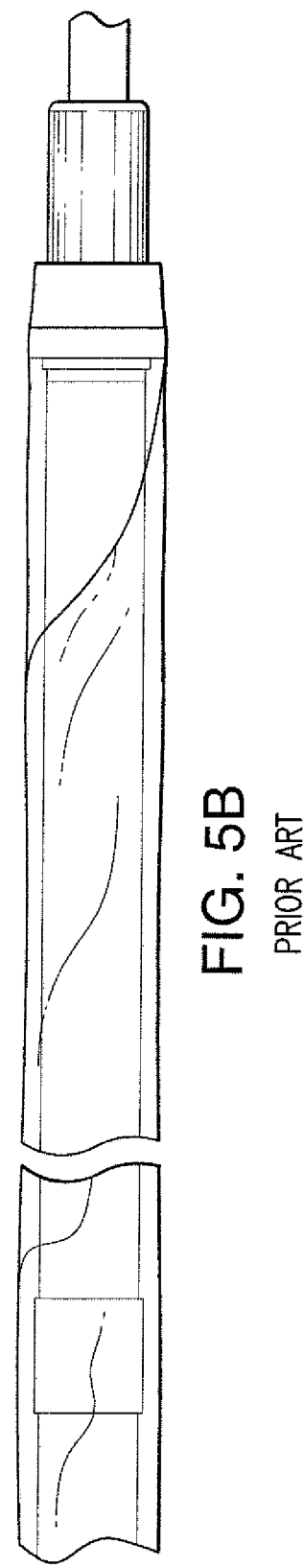
FIG. 5A
FIG. 5B
PRIOR ART

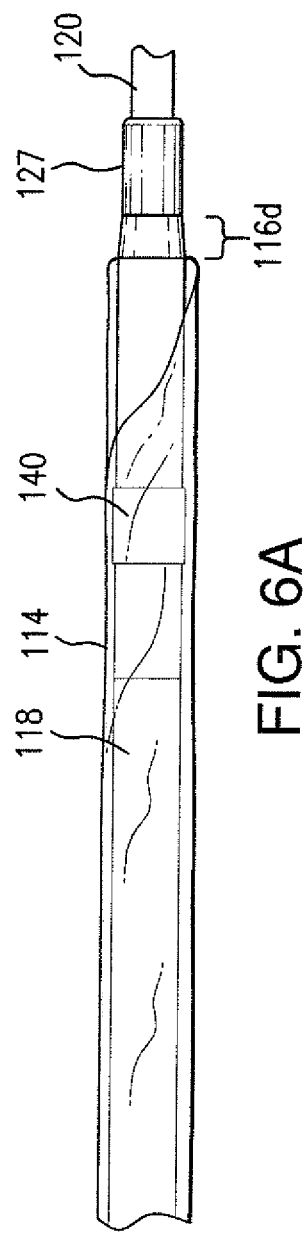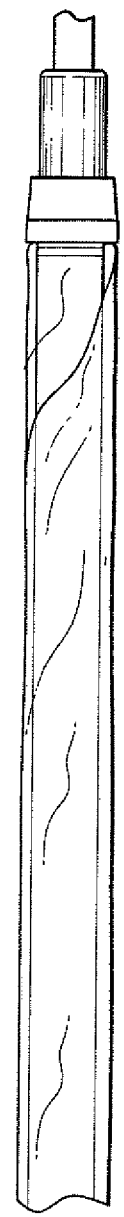
FIG. 6A
FIG. 6B
PRIOR ART

THROUGH TIP FOR CATHETER

CROSS-REFERENCE TO RELATED APPLICATION

This application claims the benefit of U.S. Provisional Patent Application Ser. No. 61/490,444, entitled "Through Tip For A Catheter" and filed on May 26, 2011, the entire content of which is incorporated herein by reference.

BACKGROUND OF THE DISCLOSED SUBJECT MATTER

Field of the Disclosed Subject Matter

The disclosed subject matter herein generally relates to medical devices, and particularly to a distal tip configuration for intracorporeal devices for therapeutic or diagnostic uses, such as balloon catheters.

Description of Related Subject Matter

In percutaneous transluminal coronary angioplasty (PTCA) procedures, a guiding catheter is advanced in the vasculature of a patient until the distal tip of the guiding catheter is seated in a desired coronary artery. A guidewire is advanced out of the distal end of the guiding catheter into the coronary artery until the distal end of the guidewire crosses a lesion to be dilated. A dilatation catheter, having an inflatable balloon on the distal portion thereof, is advanced into the coronary anatomy over the previously introduced guidewire until the balloon of the dilatation catheter is positioned across the lesion. Once positioned, the dilatation balloon is inflated with inflation fluid one or more times to a predetermined size at a suitable pressure to compress the stenosis against the arterial wall to open up the vascular passageway. Generally, the inflated diameter of the balloon is approximately the same diameter as the native diameter of the body lumen being dilated to complete the dilatation but not over expand the artery wall. After the balloon is deflated, blood resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians may additionally or alternatively implant an intravascular prosthesis inside the artery at the site of the lesion. Such stents may be bare metal, polymeric, or coated with a drug or other therapeutic agent. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter with the stent implanted within the artery at the site of the dilated lesion. Coverings on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as polyester, expanded polytetrafluoroethylene, and DACRON may be implanted in vessels to strengthen or repair the vessel, or used in an anastomosis procedure to connect vessels segments together. For details of example stents, see for example, U.S. Pat. No. 5,507,768 (Lau, et al.) and U.S. Pat. No. 5,458,615 (Klemm, et al.), which are incorporated herein by reference.

In addition to PTA, PTCA, and atherectomy procedures, balloon catheters are also used to the peripheral system such as in the veins system or the like. For instance, a balloon catheter is initially advanced over a guidewire to position the balloon adjacent a stenotic lesion. Once in place, the balloon is then inflated, and the restriction of the vessel is opened. Likewise, balloon catheters are also used for treatment of other luminal systems throughout the body.

Typically, balloon catheters comprise a hollow catheter shaft with a balloon secured at a distal end. The interior of the balloon is in a fluid flow relation with an inflation lumen extending along a length of the shaft. Fluid under pressure can thereby be supplied to the interior of the balloon through the inflation lumen. To position the balloon at the stenosed region, the catheter shaft is designed to have suitable pushability (i.e., ability to transmit force along the length of the catheter), trackability, and flexibility, to be readily advanceable within the tortuous anatomy of the vasculature. Conventional balloon catheters for intravascular procedures, such as angioplasty and stent delivery, frequently have a relatively stiff proximal shaft section to facilitate advancement of the catheter within the body lumen and a relatively flexible distal shaft section to facilitate passage through tortuous anatomy, such as distal coronary and neurological arteries, without damage to the vessel wall.

Traditional catheter shafts are often constructed with inner and outer member tubing separately with an annular space therebetween for balloon inflation. In the design of catheter shafts, it is desirable to predetermine or control characteristics such as strength, stiffness and flexibility of various sections of the catheter shaft to provide the desired catheter performance. This is conventionally performed by combining separate lengths of tubular members of different material and/or dimensions and then assembling the separate members into a single shaft length. However, the transition between sections of different stiffness or material can be a cause of undesirable kinking along the length of the catheter. Such kinking is particularly evident in rapid exchange (RX) catheters, wherein the proximal shaft section does not include the additional structure of a guidewire lumen tube. For example, a conventional RX catheter generally consists of a proximal hypotube having a single inflation lumen therethrough and a dual lumen or coaxial tube configuration at a distal end section having both a guidewire lumen and an inflation lumen therein. Known techniques to minimize kinking at the transition between the more rigid proximal section and the more flexible distal section include bonding two or more segments of different flexibility together to form the shaft. Such transition bonds need to be sufficiently strong to withstand the pulling and pushing forces on the shaft during use.

To address the described issues, catheters having varied flexibility and/or stiffness have been developed with various sections of the catheter shaft that are specifically tailored to provide the desired catheter performance. For example, each of U.S. Pat. No. 4,782,834 to Maguire and U.S. Pat. No. 5,370,655 to Burns discloses a catheter having sections along its length which are formed from materials having a different stiffness; U.S. Pat. No. 4,976,690 to Solar discloses a catheter having an intermediate waist portion which provides increased flexibility along the catheter shaft; U.S. Pat. No. 5,423,754 to Cornelius discloses a catheter having a greater flexibility at its distal portion due to both a material and dimensional transition in the shaft; U.S. Pat. No. 5,649,909 to Cornelius discloses a catheter having a proximal portion with greater stiffness due to the application of a polymeric coating thereto; and U.S. Publication No. 2010/0130925 to Haslinger discloses a multilayer catheter shaft using a combination of a high Shore D durometer value material and a lower Shore D durometer value material to reduce kinking.

Of particular interest is the configuration and bond for the distal segment or tip of the medical device or catheter. It is often desirable to provide the distal tip with a reduced crossing profile and generally atraumatic or soft configuration, yet maintain sufficient strength of the bond between the distal tip member and the balloon and/or inner tubular member to which it is attached.

Accordingly, there is a need for a catheter having a catheter shaft with an improved combination of characteristics such as strength, flexibility and ease of manufacture. The disclosed subject matter satisfies these and other needs.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve the above and other advantages and in accordance with the purpose of the disclosed subject matter, as embodied and broadly described, the disclosed subject matter includes, according to one embodiment, a catheter comprising an elongate tubular shaft having a proximal portion and a distal portion, the elongate tubular shaft including an inner tubular member having a distal length extending distally from the distal portion of the elongate tubular shaft. The elongate tubular shaft has an inflation lumen and a guidewire lumen defined therein, the guidewire lumen extending along at least the distal length of inner tubular member. The catheter further includes a distal tip member having a proximal end and a distal end, wherein the distal tip member is monolithic and the proximal end of the distal tip member is secured to a distal end of the inner tubular member, the distal tip member having a guidewire lumen in communication with the guidewire lumen of the inner tubular member. The catheter further includes a balloon having a proximal portion, a distal portion and a working length therebetween, the proximal portion of the balloon sealingly coupled to the distal portion of the elongate tubular shaft. The distal portion of the balloon is sealingly coupled to the distal tip member and the balloon defines an inner chamber in fluid communication with the inflation lumen, wherein the proximal end of the distal tip member is disposed within the inner chamber.

In accordance with another aspect of the disclosed subject matter, a method of making a balloon catheter is disclosed. The method includes providing an elongate tubular shaft having a proximal portion and a distal portion, the elongate tubular shaft including an inner tubular member having a distal length extending distally from the distal portion of the elongate tubular shaft, the elongate tubular shaft having an inflation lumen and a guidewire lumen defined therein, the guidewire lumen extending along at least the distal length of inner tubular member. The method further includes providing a distal tip member, wherein the distal tip member is monolithic and includes a proximal end and a distal end, the distal tip member having a guidewire lumen defined therethrough. The distal tip member is secured to a distal end of the inner tubular member with the guidewire lumen of the distal tip member in communication with the guidewire lumen of the inner tubular member. A balloon is provided having a proximal portion, a distal portion and a working length therebetween, the balloon defining an inner chamber therein. The method further includes coupling the proximal portion of the balloon to the distal portion of the elongate tubular shaft with the inner chamber of the balloon in fluid communication with the inflation lumen and coupling the distal portion of the balloon to the distal tip member with the proximal end of the distal tip member disposed within the interior of the balloon.

In another embodiment of the disclosed subject matter, a method of deploying a balloon catheter is disclosed. The method includes providing a catheter comprising an elongate tubular shaft having a proximal portion and a distal portion, the elongate tubular shaft including an inner tubular member having a distal length extending distally from the distal portion of the elongate tubular shaft. The elongate tubular shaft has an inflation lumen and a guidewire lumen defined therein, the guidewire lumen extending along at least the distal length of inner tubular member. The catheter further comprises a distal tip member having a proximal end and a distal end, wherein the distal tip member is monolithic and the proximal end of the distal tip member is secured to a distal end of the inner tubular member. The distal tip member has a guidewire lumen in communication with the guidewire lumen of the inner tubular member and a balloon having a proximal portion, a distal portion and a working length therebetween. The proximal portion of the balloon is sealingly coupled to the distal portion of the elongate tubular shaft, the distal portion of the balloon sealingly coupled to the distal tip member. The balloon defines an inner chamber in fluid communication with the inflation lumen, wherein the proximal end of the distal tip member is disposed within the inner chamber. The method further includes positioning the balloon of the catheter within a body lumen; and inflating the balloon by introducing pressurizing fluid through the inflation lumen of the elongate tubular shaft.

It is to be understood that both the foregoing general description and the following detailed description are embodiments and are intended to provide further explanation of the disclosed subject matter claimed. The accompanying drawings, which are incorporated in and constitute part of this specification, are included to illustrate and provide a further understanding of the system and method of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which:

FIG. 1 is a schematic side view, partially in section, of a balloon catheter embodying features of the disclosed subject matter having a distal tip member joined to an inner tubular member located within an interior of the balloon and a single central marker band.

FIG. 2A is a schematic side view, partially in section, of a balloon catheter embodying features of the disclosed subject matter having a distal tip member that tapers from the proximal end of the distal tip member to the distal end of the distal tip member.

FIG. 3 is a transverse cross sectional view of the catheter of FIG. 1, taken along lines 3-3.

FIG. 4 is a transverse cross sectional view of the catheter of FIG. 1, taken along lines 4-4.

FIGS. 5A and 5B are images for purpose of comparison between schematics of a catheter according to an embodiment of the disclosed subject matter and a conventional catheter, respectively.

FIGS. 6A and 6B are distal images of the catheter of FIGS. 5A and 5B, respectively.

DETAILED DESCRIPTION

Figure 2B:
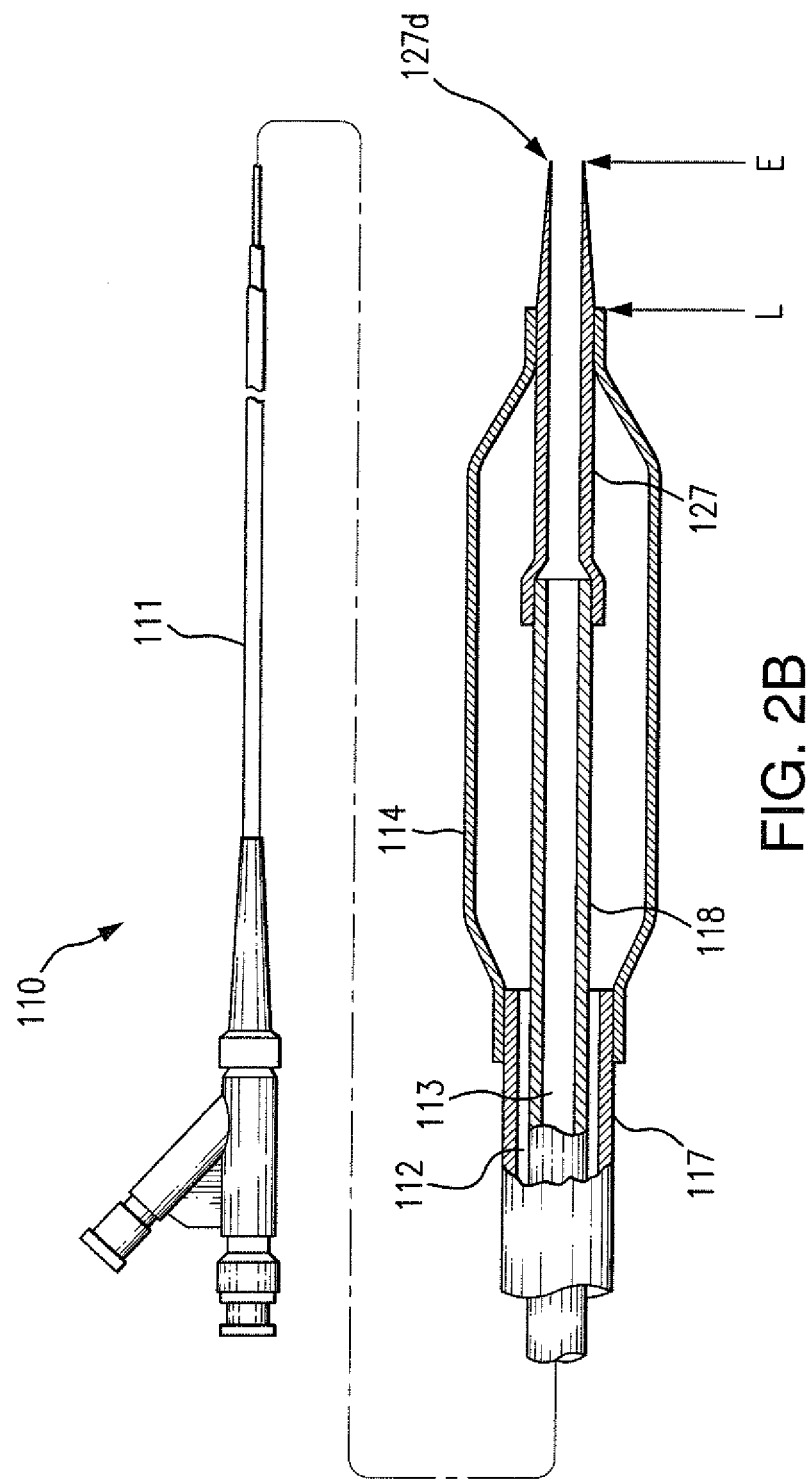
FIG. 2B is a schematic side view, partially in section, of a balloon catheter embodying features of the disclosed subject matter having a distal tip member that tapers distal to a distal end of a balloon.

Reference will now be made in detail to embodiments of the disclosed subject matter, an example of which is illustrated in the accompanying drawings. The examples are not intended to limit the scope of the disclosed subject matter in any manner. The disclosed subject matter will be described in conjunction with the detailed description of the system.

In accordance with the disclosed subject matter, a catheter is provided comprising an elongate tubular shaft having a proximal portion and a distal portion, the elongate tubular shaft including an inner tubular member having a distal length extending distally from the distal portion of the elongate tubular shaft. The elongate tubular shaft has an inflation lumen and a guidewire lumen defined therein, the guidewire lumen extending along at least the distal length of inner tubular member. The catheter further includes a distal tip member having a proximal end and a distal end, wherein the distal tip member is monolithic and the proximal end of the distal tip member is secured to a distal end of the inner tubular member, the distal tip member having a guidewire lumen in communication with the guidewire lumen of the inner tubular member. The catheter further includes a balloon having a proximal portion, a distal portion and a working length therebetween, the proximal portion of the balloon sealingly coupled to the distal portion of the elongate tubular shaft. The distal portion of the balloon is sealingly coupled to the distal tip member and the balloon defines an inner chamber in fluid communication with the inflation lumen, wherein the proximal end of the distal tip member is disposed within the inner chamber.

In accordance with another aspect of the disclosed subject matter, a method of making a balloon catheter is disclosed. The method includes providing an elongate tubular shaft having a proximal portion and a distal portion, the elongate tubular shaft including an inner tubular member having a distal length extending distally from the distal portion of the elongate tubular shaft, the elongate tubular shaft having an inflation lumen and a guidewire lumen defined therein, the guidewire lumen extending along at least the distal length of inner tubular member. The method further includes providing a distal tip member, wherein the distal tip member is monolithic and includes a proximal end and a distal end, the distal tip member having a guidewire lumen defined therethrough. The distal tip member is secured to a distal end of the inner tubular member with the guidewire lumen of the distal tip member in communication with the guidewire lumen of the inner tubular member. A balloon is provided having a proximal portion, a distal portion and a working length therebetween, the balloon defining an inner chamber therein. The method further includes coupling the proximal portion of the balloon to the distal portion of the elongate tubular shaft with the inner chamber of the balloon in fluid communication with the inflation lumen and coupling the distal portion of the balloon to the distal tip member with the proximal end of the distal tip member disposed within the interior of the balloon.

In another embodiment of the disclosed subject matter, a method of deploying a balloon catheter is disclosed. The method includes providing a catheter comprising an elongate tubular shaft having a proximal portion and a distal portion, the elongate tubular shaft including an inner tubular member having a distal length extending distally from the distal portion of the elongate tubular shaft. The elongate tubular shaft has an inflation lumen and a guidewire lumen defined therein, the guidewire lumen extending along at least the distal length of inner tubular member. The catheter further comprises a distal tip member having a proximal end and a distal end, wherein the distal tip member is monolithic and the proximal end of the distal tip member is secured to a distal end of the inner tubular member. The distal tip member has a guidewire lumen in communication with the guidewire lumen of the inner tubular member and a balloon having a proximal portion, a distal portion and a working length therebetween. The proximal portion of the balloon is sealingly coupled to the distal portion of the elongate tubular shaft, the distal portion of the balloon sealingly coupled to the distal tip member. The balloon defines an inner chamber in fluid communication with the inflation lumen, wherein the proximal end of the distal tip member is disposed within the inner chamber. The method further includes positioning the balloon of the catheter within a body lumen; and inflating the balloon by introducing pressurizing fluid through the inflation lumen of the elongate tubular shaft.

For purpose of illustration and not limitation, reference will now be made in detail to specific embodiments, examples of which are illustrated in the accompanying drawings. For the purposes of this disclosure, like reference numbers in the figures shall refer to like features unless otherwise indicated. Additionally, for purpose of understanding, the methods of the disclosed subject matter are described in conjunction with the catheter and related features.

FIG. 1 illustrates a side view, partially in section, of a balloon catheter 110 embodying features of the disclosed subject matter, generally comprising an elongate tubular shaft 111 having a proximal portion, a distal portion, an inflation lumen 112, and a guidewire lumen 113 extending at least along a portion of the length of the elongate tubular shaft.

The elongate tubular shaft of the catheter can be made of a variety of configurations. For example, the elongate tubular shaft can provide an over the wire (OTW) configuration with the guidewire lumen extending generally across the entire length of the elongate tubular shaft. In this embodiment, the elongate tubular shaft can be a single piece multi-lumen member, or can include a co-axial arrangement, as shown schematically in FIG. 1. Thus, the elongate tubular shaft can include a coaxial configuration with the inner tubular member 118 disposed within at least a length of an outer tubular member 117 such that the outer tubular member 117 and the inner tubular member 118 define the inflation lumen 112 of the elongate tubular shaft therebetween. That is, the co-axial arrangement includes outer tubular member 117 and inner tubular member 118 with the inflation lumen 112 defined therebetween. In either arrangement, i.e., multi-lumen or coaxial, the inner tubular member 118 extends beyond the distal end of the outer tubular member 117 and further defines the guidewire lumen 113, as depicted in detail in FIG. 1.

As an alternative, the catheter can be a rapid exchange (RX) configuration as known in the art, with the proximal section of the catheter comprising a proximal hypotube or the like. The distal section of the rapid exchange catheter can be a co-axial configuration as described above or a multi-lumen configuration. In the multi-lumen configuration, the distal section of the catheter comprises an elongate tubular shaft includes the inflation lumen 112 extending along the length thereof and further includes the guidewire lumen 113 extending along at least a portion of the length of the elongate tubular shaft member. The inflation lumen 112 and the guidewire lumen 113 are disposed adjacent each other. The elongate tubular shaft includes an inner tubular member 118 having a distal length extending distally from the distal portion of the elongate tubular shaft and the guidewire lumen extending along at least the distal length of inner tubular member 118. Accordingly, the elongate tubular shaft can include a multi-lumen configuration with the inner tubular member 118 defining the guidewire lumen adjacent with the inflation lumen. For purposes of discussion herein, but not limitation, an OTW configuration is depicted in FIGS. 1-7.

As embodied herein, the inner tubular member 118 can be more flexible than the outer tubular shaft member 117, although it is not necessary for the inner tubular member 118 to be more flexible than the outer tubular shaft member 117. For example, in accordance with another embodiment, only the portion of the inner tubular member extending distal of the outer tubular member can have greater flexibility than the outer tubular member. Furthermore, the inner member can have a variety of suitable configurations including being a single unitary tube, or multiple tubes joined by end-to-end joints, butt joints, or lap joints.

In accordance with the disclosed subject matter, a distal tip member 127 is depicted in FIG. 1. The distal tip member is a monolithic member and has a proximal end 127P and a distal end 127D. The proximal end 127P of the distal tip member 127 is secured to a distal end 127D of the inner tubular member 118. The distal tip member embodied herein has a guidewire lumen 213 defined therethrough and coupled in communication with the guidewire lumen 113 of the inner tubular member 118.

The distal tip member 127 can have a variety of suitable configurations. In one embodiment, as depicted in FIG. 1 for illustration, the distal tip member can have a generally cylindrical configuration with uniform diameter and wall thickness. Alternatively, and as depicted in FIG. 2A, the distal tip member can have a distally decreasing cross-dimension, such as a taper from the proximal end of the distal tip member to the distal end of the distal tip member. In this embodiment, the distal tip member has a substantially constant taper from the proximal end to the distal end.

For example, and with reference to a coronary dilatation catheter, the distal tip member can also have a uniform or varying profile along a length of the distal tip member. The outer cross-dimension of the distal tip member can decrease in a distal direction between the proximal end and the distal end. For example, the outer cross-sectional dimension or profile of the distal tip member at a position immediately distal of a distal end of the balloon at location L can range between approximately 0.018 inches to approximately 0.028 inches. In one example, the cross-sectional profile of the distal tip member is approximately 0.023 inches at the position immediately distal to the distal end of the balloon. In contrast, the distal end of the distal tip member can comprise a cross-sectional dimension or profile at location E between approximately 0.012 inches to approximately 0.028 inches. In one example, the cross-sectional profile of the distal tip is approximately 0.017 inches at the distal end of the distal tip member for a 3.0×20 mm balloon.

In another embodiment as depicted in FIG. 2B, the distal tip member can taper distal to a distal end of a balloon 114 at location L only. For example, and solely for purposes of illustration, FIG. 2B depicts a distal tip member having a uniform profile between a proximal end of the distal tip member to the location L, and then a decreasing profile distally therefrom. That is from the proximal end of the distal tip member to the position L which is immediately distal to the distal end of the balloon, the distal tip member comprises a substantially uniform cross-sectional profile. However, from location L to the distal end of the distal tip member at location E, the distal tip member 127 tapers beyond the distal end of the balloon. In one example with an inflated balloon of 3.0 mm for coronary dilatation, the outer cross-sectional dimension or profile of the distal tip member 127 at location L can be approximately 0.021" and the entry profile of the distal tip member 127 at location E can be approximately 0.017" for a 3×20 mm balloon. The crossing profile measurement of the distal tip member is taken at the distal edge of the distal balloon seal.

The distal tip member can have a variety of suitable cross-sectional shapes and configurations. In the embodiments of FIG. 2A and 2B, the distal tip member comprises a substantially circular cross-sectional, configuration. For example, and with reference to a coronary dilatation catheter, an inner diameter of the distal tip member can range from approximately 0.008 inches to approximately 0.038 inches and an outer diameter of the distal tip member can range from approximately 0.014 inches to approximately 0.045 inches.

In this embodiment, the distal tip member can have a wall thickness less than or equal to approximately 0.006 inches. In the embodiment as depicted in FIG. 2B, the distal tip member further includes a wall thickness that decreases in a distal direction.

Again with reference to a coronary dilatation catheter for purpose of illustration and not limitation, the distal tip member can comprise a length of up to approximately 5 mm. In one embodiment, the distal tip member is approximately 3 mm. The distal tip member can extend a suitable length distal to the distal end of the balloon. For example, the distal tip member extends up to approximately 2 mm distal from a distal end of the balloon.

The distal end of the distal tip member 127 can comprise a rounded configuration or a blunt configuration for enhanced lumen crossing. The rounded tip configuration can be formed by laser, milling or other suitable techniques. Other embodiments of suitable tip configuration can be used, such as those described herein are also described in U.S. Application No. 11/958,106; U.S. Pat. No. 7,862,541; U.S. application Ser. No. 12/983,504; U.S. Pat. No. 7,549,975; U.S. patent application Ser. No. 12/468,745; U.S. Pat. No. 6,964,750; and U.S. patent application Ser. No. 11/241,936, the contents of which are herein incorporated by reference in their entirety.

The distal tip member can be coupled to the elongate tubular shaft in a plurality of suitable ways. For purposes of example, the distal tip member can be coupled to the inner tubular member by a butt joint 126 or by a lap joint 128 as shown with respect to FIG. 2A and 2B, respectively. Other suitable junctures and joints likewise can be used. As depicted in FIG. 2B, the distal tip member and the inner tubular member are coextensive with each other. The distal tip member is generally configured to provide flexibility and is typically formed of a softer polymeric material than the adjacent section of the inner tubular member. In this manner, the softer distal tip member can be overlapped with the outer surface of the inner tubular member and bonded thereto or the distal tip member can overlap the outer surface of the inner tubular member and bonded thereto.

The distal tip member can include a plurality of suitable materials. For example, the distal tip member can be formed of a variety of suitable polymeric materials. For example, it can be desirable for the surface of the tip member to be compatible for fusion or thermal bonding with the material of the balloon and/or inner tubular member, as further discussed here. In one embodiment, the distal tip member is made of polyether block amide (PEBAX) or block copolymer or a thermoplastic. The relatively low Shore durometer hardness of the soft distal tip material can range from about 55D to 72D. In one embodiment, the distal tip member is formed at least in part of a softer polymeric material than a distal end portion of the inner tubular member immediately proximally adjacent to the distal tip member. The distal tip member is softer and more flexible than the inner tubular member as a whole. In this manner, the distal tip member 127 can be formed of a relatively soft polymeric material to provide an atraumatic distal leading end for the catheter.

In some embodiments, the distal tip member is a single layer tubular member, such as a polymer capable of fusion bond with an adjacent layer of the inner tubular member 118 and/or the balloon. Alternatively, a multilayer configuration can be used with the exposed layers compatible for fusion or thermal bonding with the material to be joined, e.g., the inner tubular member and/or the balloon. If the material of the distal tip member is not compatible for fusion or thermal bonding, then other conventional bonding or joining techniques can be used, such as adhesives or the like.

The distal tip member 127 provides for a flexible, ultra low profile for superb deliverability. The low crossing profile allows for easier access to complex lesions. In this manner, the catheter can be advanced within a vasculature to position the balloon at a desired location.

The catheter according to embodiments of the disclosed subject matter can also include a coating, such as a hydrophilic coating. For example, in one embodiment, at least an exterior of the distal tip member includes a coating. Such hydrophilic coatings are described in U.S. Publication 2010/0285085 and U.S. Publication 2010/0189876, the contents of which are herein incorporated by reference in their entirety.

As discussed above, the catheter further includes a balloon having a deflated condition and an inflated condition. The balloon generally includes a proximal portion, a distal portion and a working length therebetween. The proximal portion of the balloon is sealingly coupled to the distal portion of the elongate tubular shaft and the distal portion of the balloon is sealingly coupled to the distal tip member such that the proximal end of the distal tip member is disposed within the inner chamber. The balloon defines an inner chamber in fluid communication with the inflation lumen.

For example, and with reference to FIG. 1, the proximal balloon 114 includes a proximal skirt section 116p, a proximal cone section 115p, a distal cone section 115d, and a distal skirt section 116d. The balloon 114 includes a working length between the proximal cone section 115p and the distal cone section 115d. As illustrated herein, the proximal skirt section is sealingly secured to the elongate tubular shaft member. In the embodiment of FIG. 1, the proximal skirt section 116p is coupled to the outer tubular member 117. The distal skirt section 116d is sealingly secured to the distal tip member 127. The inner chamber 141 of the balloon is defined between the proximal skirt section 116p and the distal skirt section 116d of the balloon. The inner chamber is coupled to the elongate tubular shaft in fluid communication with the inflation lumen 112. As illustrated in FIG. 1, the proximal end 127P of the distal tip member within the inner chamber is coupled with the inner tubular member 118. Accordingly, the distal skirt section 116d is disposed distal to the proximal end 127P of the distal tip member 127.

FIG. 3 is a cross-section of the catheter 110 of FIG. 1 along the lines 3-3. In FIG. 3, the distal tip member 127 defines the guidewire lumen 213 with the guidewire 120 extending therethrough. The balloon 114 is in an inflated condition and the distal cone 115d extends radially outwardly from the distal tip member 127.

FIG. 4 is a cross-section of the catheter 110 of FIG. 1 along the lines 4-4. In FIG. 4, the distal skirt section 116d is sealingly secured to the distal tip member 127. The distal tip member 127 further defines the guidewire lumen 213 with the guidewire 120 extending therethrough.

The proximal end 127P of the distal tip member can be disposed at a suitable location within the inner chamber of the balloon, as desired. For example, in one embodiment, the proximal end 127P can be located proximate to the distal skirt section 116d such as for a stent delivery system or the like. In another embodiment, the proximal end 127P is spaced proximally from the distal end of the balloon, as shown in FIG. 2A and FIG. 2B, such as for a dilatation balloon catheter. Generally, the joint or juncture between the inner tubular member and the proximal end of the distal tip member is located at or distal to the center of the balloon interior. The location of the proximal end 127P within the balloon 114 allows for a smoother gradual transition for the catheter 110, as compared with conventional catheters.

FIG. 5A depicts a catheter according to an embodiment of the disclosed subject matter whereas FIG. 5B depicts a known catheter. In FIG. 5A, the catheter includes a gradual transition between a distal end portion of the inner tubular member 118 and the proximal end portion of the distal tip member 127. FIG. 5A depicts the inner tubular member 118 coupled to the distal tip member 127 within the inner chamber of the balloon 114 with a guidewire 120 disposed therethough. A radiopaque marker 140 is disposed on the tip member 127. The distal skirt section 116d of the balloon is disposed on the distal tip member distal to the proximal end of the distal tip member 127. This gradual transition is accomplished by one or more of the coextensive length of the inner tubular member and the distal tip member, the location of the juncture within the inner chamber of the balloon, the tapered shape of the distal tip member, the use of a softer material of the distal tip member than the inner tubular member, and/or an increased length of the distal tip member. In contrast, FIG. 5B shows an abrupt shift of an inner member to a tip. Such known configuration promotes stiffness at the distal portion of the catheter and kinking of the catheter when moving through tortuous paths.

FIGS. 6A and 6B depict distal views the catheters of FIGS. 5A and 5B, respectively, with reference to the catheter in accordance with the disclosed subject matter herein. In FIG. 6A, the junction of the inner tubular member 118 to the distal tip member 127 is disposed within the inner chamber of the balloon 114 and spaced proximally from the junction of the distal tip member 127 to the distal portion of the balloon 114 at the distal skirt section 116d. This proximal spacing allows for a gradual transition of the catheter to enhance flexibility and prevent kinking. A radiopaque marker 140 is disposed on the distal tip member 127 in FIG. 6A. By contrast, and with reference to a conventional catheter as shown in FIG. 6B, the junction of the inner member to the tip is located at the junction of the distal end of the balloon to the inner member. Such configuration as depicted in FIG. 5B and 6B creates an abrupt and less flexible transition.

Figure 7:
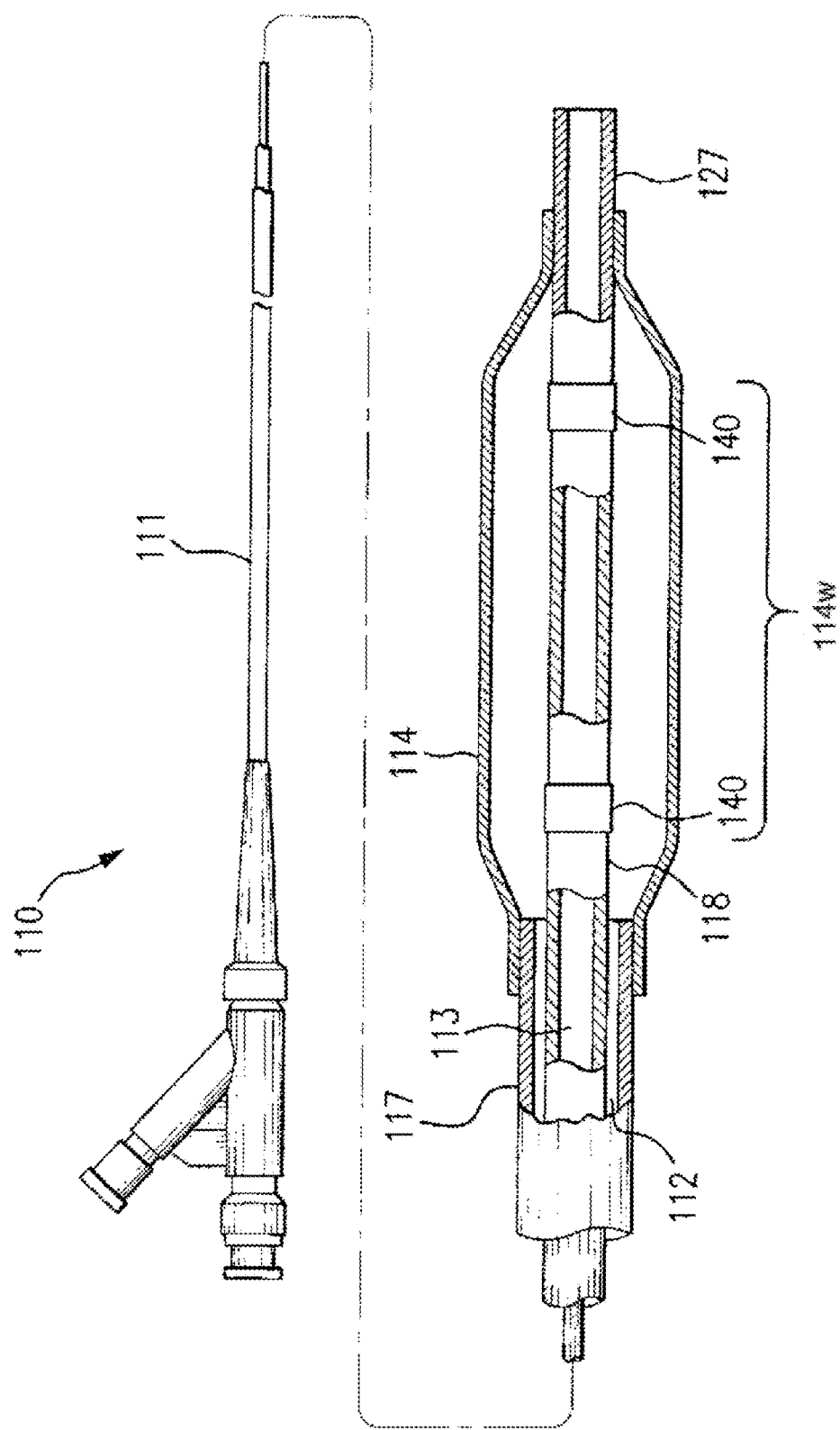
FIG. 7 is a schematic side view, partially in section, of an over the wire balloon catheter embodying features of the disclosed subject matter having a distal tip member joined to an inner tubular member located within an interior of the balloon and two marker bands.

As further depicted in FIGS. 1 and 7, and in accordance with another aspect of the disclosed subject matter, the catheter can include at least one radiopaque marker. The radiopaque marker can be coupled to the inner tubular member. The marker can be made of radiopaque material, such as metal or a radiopaque loaded polymer such as disclosed in U.S. Ser. No. 11/455,382, which is incorporated herein by reference in its entirety.

The location of the markers can depend on the size of the balloon. For example, in embodiments having smaller balloons, one radiopaque marker can be used as depicted in FIG. 1. In embodiments where one radiopaque marker is used, the marker can be located in the center of the inflatable working length 114w. However, radiopaque markers can be provided at a variety of locations including at the ends of the working length section depending on the size of the balloon.

FIG. 7 depicts another arrangement of the at least one marker coupled to the inner tubular member of the catheter. The catheter 110 has two radiopaque markers 140 located on the inner tubular member 118 within the inner chamber 141 of the balloon 114 and along the working length 114w of the balloon 114. In this embodiment, the markers 140 are generally aligned with the proximal and distal cone sections 114c to define the working length 114w of the balloon therebetween.

Further embodiments of catheters having marker configurations are described in U.S. application Ser. Nos. 11/775,480; 12/945,566; U.S. Pat. No. 7,862,541; application Ser. No. 12/983,504; U.S. Pat. No. 7,549,975; U.S. patent application Ser. No. 12/468,745; U.S. Pat. No. 6,964,750; U.S. application Ser. No. 11/455,382; U.S. Pat. Nos. 7,833,597; 7,322,959; 7,303,798; U.S. application Ser. Nos. 11/775,480; 12/945,566; U.S. Publication 2010/0285085; U.S. Publication 2010/0189876; and U.S. patent application Ser. No. 11/241,936; the contents of which are herein incorporated by reference in their entirety.

The catheter can further includes a medical device is coupled to the balloon. An example of a medical device includes stents and other suitable devices and implants likewise delivered using the catheter and method. For details of example stents, see for example, U.S. Pat. No. 5,507,768 (Lau, et al.) and U.S. Pat. No. 5,458,615 (Klemm, et al.), which are incorporated herein by reference.

The elongate tubular shaft member including the outer tubular member and the inner tubular member can have a multilayered configuration with a layer of material readily bondable. For example, the inner tubular member can have an outer layer of a material such as a polyamide which facilitates bonding to adjacent components, and an inner layer of a lubricious/low friction material such as HDPE.

In another embodiment, the inner tubular member is a trilayer tubular member having an inner layer typically formed of a lubricous material such as HDPE, a middle tie layer such as a functionalized polyolefin adhesive polymer, and an outer readily bondable layer such as a polyamide such as a nylon or a polyether block amide (PEBAX).

In the embodiment as depicted in FIG. 1, the balloon 114 is depicted as a single layer balloon. However, multilayered balloons are contemplated herein. An example of a multilayered balloon for a catheter is described in U.S. Pat. No. 7,828,766 and U.S. application Ser. No. 12/897,202, the contents of which are herein incorporated by reference in their entirety. Further, various embodiments of catheters with other balloon configurations are described in U.S. Pat. No. 6,923,822; U.S. application Ser. No. 11/189,536; U.S. Publication Nos. 2009/0036829 and 2007/0021772, the contents of which are herein incorporated by reference in their entirety.

The dimensions of catheters of the disclosed subject matter are determined largely by the size of the balloon and guidewire to be employed, the catheter type, and the size of the artery or other body lumen through which the catheter must pass, or the size of the stent being delivered. For example, the outer tubular member 117 can have an outer diameter of about 0.025 to about 0.04 inch (0.064 to 0.10 cm), in some embodiments about 0.037 inch (0.094 cm), and the wall thickness of the outer tubular member 117 can vary from about 0.002 to about 0.008 inch (0.0051 to 0.02 cm), in some embodiments about 0.003 to 0.005 inch (0.0076 to 0.013 cm). The inner tubular member 118 typically has an inner diameter of about 0.01 to about 0.018 inch (0.025 to 0.046 cm), in some embodiments about 0.016 inch (0.04 cm), and a wall thickness of about 0.004 to about 0.008 inch (0.01 to 0.02 cm). The overall length of the catheter 110 may range from about 100 to about 150 cm, and in some embodiments about 143 cm. The balloon 114 can have a length about 0.8 cm to about 6 cm (0.315 inches to 2.362 inches), and an inflated working diameter of about 0.5 to about 10 mm (0.0197 to 0.3937 inches). The distal tip member 127 can range from 1 mm to 35 mm in length and an inner diameter of about 0.010 to about 0.035 inch (0.025 to 0.046 cm), in some embodiments about 0.016 inch (0.04 cm), and a wall thickness of about 0.004 to about 0.008 inch (0.01 to 0.02 cm). Other dimensions are herein contemplated and the above dimensions are provided as examples only.

Although the tubular members of the elongate tubular shafts 111 are illustrated as having uniform inner and outer diameters and wall thicknesses, each or both of these members can be provided with tapering inner and/or outer diameters at various locations along the length of the elongate tubular shaft. The inner tubular member 118 can be provided with a tapered distal end (i.e., which decreases the outer diameter of the tubular member by tapering uniformly around the entire circumference of the tubular member), and the proximal end of the soft tip member can overlap the tapered distal end for bonding thereto. Furthermore and for example, the tip member 127 can have a thinner wall thickness than the end section of the inner tubular member to be bonded thereto, in which case the inner surfaces can be aligned and the outer surface of the inner member is caused to flow distally during bonding to smooth the outer surface at the junction.

In accordance with another aspect of the disclosed subject matter, a method of making a balloon catheter is disclosed. The method includes providing an elongate tubular shaft having a proximal portion and a distal portion, the elongate tubular shaft including an inner tubular member having a distal length extending distally from the distal portion of the elongate tubular shaft, the elongate tubular shaft having an inflation lumen and a guidewire lumen defined therein, the guidewire lumen extending along at least the distal length of inner tubular member. The method further includes providing a distal tip member, wherein the distal tip member is monolithic and includes a proximal end and a distal end, the distal tip member having a guidewire lumen defined therethrough. The distal tip member is secured to a distal end of the inner tubular member with the guidewire lumen of the distal tip member in communication with the guidewire lumen of the inner tubular member. A balloon is provided having a proximal portion, a distal portion and a working length therebetween, the balloon defining an inner chamber therein. The method further includes coupling the proximal portion of the balloon to the distal portion of the elongate tubular shaft with the inner chamber of the balloon in fluid communication with the inflation lumen and coupling the distal portion of the balloon to the distal tip member with the proximal end of the distal tip member disposed within the interior of the balloon.

A variety of techniques can be used to couple or otherwise form the junction or junctures of the catheter disclosed herein. For example, reference is made to the juncture between the balloon and the distal tip member. To couple the distal portion of the balloon to the distal tip member, a shrink wrap can be provided over at least a portion of the distal portion of the balloon and the distal tip member. At least the portion of the distal portion of the balloon is thermally bonded to the distal tip member using a laser or the like. For example, the laser can be passed in a helical manner relative the outer surface of the distal tip member along the longitudinal axis thereof. In this manner, the material of the distal portion of the balloon and of the distal tip member will soften and melt. As the laser is moved distally, in a helical fashion about the longitudinal axis of the tip member, the softer and/or molten material will be urged in a distal direction to form a tapered shape beneath the shrink wrap. Once completed, the shrink wrap can be removed. The distal end of the distal tip member can be rounded or otherwise shaped to form a less traumatic end using a laser, milling or other process.

Likewise, when bonding the proximal end of the distal tip member to the inner tubular member, a mandrel can be provided inside the tubular members 118, 127 to support the luminal shape. Heat shrink tube (not shown) or the like can be provided on the tubular members 118, 127 at the location of the mating or coupled surfaces, to facilitate a smooth transition along the juncture during bonding. The shrink tube and mandrel are removed after formation of the bond.

The elongate tubular shaft outer and inner tubular members and tip member can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as, but not limited to, by fusion bonding or use of adhesives. The inner tubular member and outer tubular member can be multilayered tubing, or sections of tubing joined end-to-end, as is conventionally known for balloon catheter shafts. Although the elongate tubular shaft is illustrated as having an inner and outer tubular member, a variety of suitable shaft configurations can be used including a multi-lumen extruded shaft having a side-by-side lumens extruded therein. For rapid exchange configurations, the outer tubular member can further include supporting members including a high strength member such as a hypotube in the proximal shaft section and/or across the guidewire proximal port in the rapid exchange embodiment (not shown). Example configurations are disclosed in U.S. Pat. No. 7,906,066, the subject matter of which is incorporated herein by reference in its entirety.

During manufacture, the balloon can be formed using conventional techniques and bonded to the distal tip member by at least one of laser bond or heat fusion. The distal cone of the balloon can be cooled during heat fusion bonding of the distal skirt section of the balloon to the underlying section of the distal tip member, for example by directing a cooling fluid (e.g., air stream) at the distal cone. Prior to bonding, the distal skirt section 116 of the balloon can have an inner diameter closely matched to the outer diameter of the distal tip member, the distal tip member 127, such that the resulting distal skirt section seal has a low profile. During assembly, the distal tip member 127 is disposed within the distal skirt section 116*d*. With the distal tip member 127 thus in position under the distal skirt 116*d*, the bond between the distal skirt 116*d* and distal tip 127 is formed as described herein. Various embodiments of catheters with other balloon configurations are described in U.S. Pat. No. 6,923,822; U.S. application Ser. No. 11/189,536; U.S. Publication Nos. 2009/0036829 and 2007/0021772, the contents of which are herein incorporated by reference in their entirety. An example of a multilayered balloon for a catheter is described in U.S. Pat. No. 7,828,766 and U.S. application Ser. No. 12/897,202, the contents of which are herein incorporated by reference in their entirety.

In another embodiment of the disclosed subject matter, a method of deploying a balloon catheter is disclosed. The method includes providing a catheter comprising an elongate tubular shaft having a proximal portion and a distal portion, the elongate tubular shaft including an inner tubular member having a distal length extending distally from the distal portion of the elongate tubular shaft. The elongate tubular shaft has an inflation lumen and a guidewire lumen defined therein, the guidewire lumen extending along at least the distal length of inner tubular member. The catheter further comprises a distal tip member having a proximal end and a distal end, wherein the distal tip member is monolithic and the proximal end of the distal tip member is secured to a distal end of the inner tubular member. The distal tip member has a guidewire lumen in communication with the guidewire lumen of the inner tubular member and a balloon having a proximal portion, a distal portion and a working length therebetween. The proximal portion of the balloon is sealingly coupled to the distal portion of the elongate tubular shaft, the distal portion of the balloon sealingly coupled to the distal tip member. The balloon defines an inner chamber in fluid communication with the inflation lumen, wherein the proximal end of the distal tip member is disposed within the inner chamber. The method further includes positioning the balloon of the catheter within a body lumen; and inflating the balloon by introducing pressurizing fluid through the inflation lumen of the elongate tubular shaft.

While the present disclosed subject matter is described herein in terms of certain embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

It will be understood that the above description of the present disclosed subject matter is susceptible to various modifications, changes and adaptations, and the same are intended to be comprehended within the meaning and range of equivalents of the appended claims.

What is claimed is:

1. A catheter comprising:
an elongate tubular shaft having a proximal portion and a distal portion, the elongate tubular shaft including an inner tubular member having a distal length extending distally from the distal portion of the elongate tubular shaft, the elongate tubular shaft having an inflation lumen and a guidewire lumen defined therein, the guidewire lumen extending along at least the distal length of the inner tubular member;
a distal tip member having a proximal end and a distal end, wherein the distal tip member is monolithic and the proximal end of the distal tip member is secured to a distal end of the inner tubular member, the distal tip member having a guidewire lumen in communication with the guidewire lumen of the inner tubular member; and
a balloon having a proximal cone section, a distal cone section and a working length between the proximal cone section and the distal cone section, a proximal portion of the balloon sealingly coupled to the distal portion of the elongate tubular shaft and a distal portion of the balloon sealingly coupled to the distal tip member, the balloon defining an inner chamber in fluid communication with the inflation lumen;
wherein the proximal end of the distal tip member and the distal end of the inner tubular member are disposed within the inner chamber along the working length of the balloon, the distal tip member having a uniform cross-sectional profile between a location where the distal tip member is secured to the distal end of the inner tubular member and a location distal of a distal end of the balloon, the distal tip member further haying a decreased cross-sectional profile distal of the location distal of the distal end of the balloon; and wherein the distal tip member has a substantially constant taper from immediately distal of the distal end at the balloon to the distal end of the distal tip member.

2. The catheter according to claim 1, wherein an outer cross-dimension of the distal tip member decreases in a distal direction from immediately distal of the distal end of the balloon to the distal end of the distal tip member.

3. The catheter according to claim 1, wherein the distal tip member tapers distal of the distal end of the balloon.

4. The catheter according to claim 1, wherein the distal tip member has an outer cross-dimension at a position immediately distal of the distal end of the balloon between approximately 0.018 inches to approximately 0.028 inches and the distal end of the distal tip member comprises an outer cross-dimension of between approximately 0.012 inches to approximately 0.022 inches.

5. The catheter according to claim 1, wherein the distal tip member has an inner diameter between 0.010 inches to approximately 0.035 inches.

6. The catheter according to claim 1, wherein a wall thickness of the distal tip member decreases in a distal direction.

7. The catheter according to claim 1, wherein the distal tip member has a wall thickness less than or equal to approximately 0.006 inches.

8. The catheter according to claim 1, wherein the distal tip member has a length of up to approximately 5 mm.

9. The catheter according to claim 1, wherein the distal tip member extends approximately 2 mm distal to the distal end of the balloon.

10. The catheter according to claim 1, wherein the distal end of the distal tip member comprises at least one of a rounded configuration or a blunt configuration.

11. The catheter according to claim 1, wherein the distal tip member and the inner tubular member are coupled by at least one of a lap-joint or a butt-joint.

12. The catheter according to claim 1, wherein the distal tip member includes a material having a Shore durometer hardness between approximately 55 D to approximately 72 D.

13. The catheter according to claim 1, wherein the distal tip member includes at least one of a block copolymer or a thermoplastic.

14. The catheter according to claim 1, wherein an exterior of the distal tip member includes a coating.

15. The catheter according to claim 1, wherein the balloon is bonded to the distal tip member by at least one of laser bond or heat fusion.

16. The catheter according to claim 1, wherein the distal portion of the balloon includes a distal skirt section disposed distal to the proximal end of the distal tip member.

17. The catheter according to claim 1, further comprising at least one radiopaque marker coupled to the inner tubular member.

18. The catheter according to claim 1, further comprising a medical device coupled to the balloon.

19. The catheter according to claim 1, wherein the elongate tubular shaft includes a coaxial configuration with the inner tubular member disposed within at least a length of an outer tubular member, the outer tubular member and the inner tubular member defining the inflation lumen of the elongate tubular shaft therebetween.

20. The catheter according to claim 1, wherein the elongate tubular shaft includes a multi-lumen configuration with the inner tubular member defining the guidewire lumen adjacent with the inflation lumen.

21. The catheter according to claim 1, wherein the proximal end of the distal tip member is located at or distal to a center of the inner chamber.

22. A method of making a balloon catheter, comprising:
providing an elongate tubular shaft having a proximal portion and a distal portion, the
elongate tubular shaft including an inner tubular member having a distal length extending distally from the distal portion of the elongate tubular shaft, the elongate tubular shaft having an inflation lumen and a guidewire lumen defined therein, the guidewire lumen extending along at least the distal length of inner tubular member; providing a distal tip member, wherein the distal tip member is monolithic and includes a proximal end and a distal end, the distal tip member having a guidewire lumen defined therethrough; securing the distal tip member to a distal end of the inner tubular member with the guidewire lumen of the distal tip member in communication with the guidewire lumen of the inner tubular member; providing a balloon having a proximal cone section, a distal cone section-and a working length between the proximal cone section and the distal cone section, the balloon defining an inner chamber therein; coupling a proximal portion of the balloon to the distal portion of the elongate tubular shaft with the inner chamber of the balloon in fluid communication with the inflation lumen; and coupling a distal portion of the balloon to the distal tip member with the proximal end of the distal tip member disposed within the inner chamber along the working length of the balloon, the distal tip member having a uniform cross-sectional profile between a location where the distal tip member is secured to the distal end of the inner tubular member and a location distal of a distal end of the balloon and a decreased cross-sectional profile distal of the location distal of the distal end of the balloon; and wherein the distal tip member has a substantially constant taper immediately distal of the distal end of the balloon to the distal end of the distal tip member.

23. The method of claim 22, wherein the coupling the distal portion of the balloon to the distal tip member includes
providing a shrink wrap over at least a portion of the distal portion of the balloon and the distal tip member;
thermally bonding at least the portion of the distal portion of the balloon to the distal tip member; and
removing the shrink wrap.

24. The method of claim 22, further comprising rounding the distal end of the distal tip member.

25. The method of claim 22, further comprising tapering the distal tip member between the location immediately distal of the distal end of the balloon to the distal end.

* * * * *